United States Patent [19]

Szycher et al.

[11] Patent Number: 4,880,690

[45] Date of Patent: * Nov. 14, 1989

[54] PERFUME PATCH

[75] Inventors: Michael Szycher, Lynnfield; Jonathan L. Rolfe, North Easton, both of Mass.

[73] Assignee: Thermedics, Inc., Woburn, Mass.

[*] Notice: The portion of the term of this patent subsequent to Sep. 30, 2003 has been disclaimed.

[21] Appl. No.: 243,152

[22] Filed: Sep. 9, 1988

Related U.S. Application Data

[63] Continuation of Ser. No. 95,055, Sep. 9, 1987, abandoned, which is a continuation-in-part of Ser. No. 932,696, Nov. 19, 1986, abandoned, which is a continuation-in-part of Ser. No. 768,623, Aug. 23, 1985, Pat. No. 4,638,043, which is a continuation-in-part of Ser. No. 726,809, Apr. 25, 1985, abandoned, which is a continuation-in-part of Ser. No. 670,810, Nov. 13, 1984, Pat. No. 4,614,787.

[51] Int. Cl.$^4$ .............. D03D 3/00; B32B 7/02; D04B 1/02; A01N 25/26

[52] U.S. Cl. .................. 428/224; 428/225; 428/246; 428/247; 428/262; 428/905; 424/76.3; 424/76.4; 424/78; 424/486; 512/4

[58] Field of Search ............. 528/75; 604/304, 372; 424/16, 486, 78, 76.3, 76.4; 252/522 A; 428/224, 225, 246, 247, 262, 905

[56] References Cited

U.S. PATENT DOCUMENTS

| | | | |
|---|---|---|---|
| 3,062,210 | 11/1962 | Scholl | 128/156 |
| 3,303,046 | 2/1967 | Chebiniak et al. | 117/36.1 |
| 3,342,183 | 9/1967 | Edenbaum | 128/268 |
| 3,374,134 | 3/1968 | Waldman | 156/239 |
| 3,526,224 | 9/1970 | Potts | 128/156 |
| 3,567,119 | 3/1971 | Wilbert et al. | 239/6 |
| 3,570,482 | 3/1971 | Emoto et al. | 128/156 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,842,832 | 10/1974 | Wideman et al. | 128/169 |
| 3,844,478 | 2/1974 | Davis | 528/75 |
| 3,870,593 | 3/1975 | Elton et al. | 161/159 |
| 3,881,473 | 5/1975 | Corvi et al. | 128/90 |
| 3,949,742 | 4/1976 | Nowakowski | 128/155 |
| 3,975,567 | 8/1976 | Lock | 428/315 |
| 4,034,759 | 7/1977 | Hung | 128/156 |
| 4,038,239 | 7/1977 | Coyner et al. | 528/75 |
| 4,051,848 | 10/1977 | Levine | 128/156 |
| 4,144,317 | 3/1979 | Higuchi et al. | 424/21 |
| 4,156,067 | 5/1979 | Gould | 528/73 |
| 4,189,467 | 2/1980 | Von Bittera et al. | 424/14 |
| 4,209,605 | 6/1980 | Hoy et al. | 528/54 |
| 4,215,684 | 8/1980 | Westip | 128/156 |
| 4,226,944 | 10/1980 | Stone et al. | 521/76 |
| 4,233,969 | 11/1980 | Lock et al. | 128/156 |
| 4,236,550 | 12/1980 | Braun et al. | 139/421 |

(List continued on next page.)

FOREIGN PATENT DOCUMENTS

| | | |
|---|---|---|
| 0110678 | 11/1983 | European Pat. Off. |
| 0114581 | 1/1984 | European Pat. Off. |
| 0188883 | 6/1988 | European Pat. Off. |
| 2928591 | 2/1981 | Fed. Rep. of Germany |
| 1598644 | 8/1970 | France |
| 1476894 | 4/1975 | United Kingdom |
| 2034728 | 10/1979 | United Kingdom |
| 2093702 | 9/1982 | United Kingdom |

*Primary Examiner*—John Kight
*Assistant Examiner*—Nathan M. Nutter
*Attorney, Agent, or Firm*—Lorusso & Loud

[57] ABSTRACT

A perfume patch comprising a fragrance-emitting member having a fragrance dispersed within an ultra-thin polyurethane membrane. A layer of pressure sensitive adhesive is applied to adhere the member to a surface. The polyurethane is formed from a diisocyanate, a macroglycol, and an acrylyl chain terminator to which a photoinitiator and a fragrance oil are added prior to curing. A barrier layer may be applied by an adhesive or other suitable means to prevent migration of the fragrance oil to the adhesive so that no residue of adhesive remains on the surface. The perfume patch preferably includes a support for the fragrance-emitting member for ease in application and handling.

27 Claims, 3 Drawing Sheets

U.S. PATENT DOCUMENTS

| | | | |
|---|---|---|---|
| 4,254,179 | 3/1981 | Carson III et al. | 428/311 |
| 4,257,176 | 3/1981 | Hartung et al. | 326/44 |
| 4,264,757 | 4/1981 | Park | 528/75 |
| 4,305,551 | 12/1981 | Hymes et al. | 128/156 |
| 4,307,717 | 12/1981 | Hymes et al. | 128/156 |
| 4,308,184 | 12/1981 | Thoma et al. | 428/904 X |
| 4,321,117 | 3/1982 | Kaetsu et al. | 521/28 |
| 4,331,135 | 5/1982 | Westip | 128/156 |
| 4,336,243 | 6/1982 | Sanvordeker | 424/28 |
| 4,340,043 | 7/1982 | Seymour | 128/132 |
| 4,341,207 | 7/1982 | Steer et al. | 128/155 |
| 4,391,106 | 7/1983 | Schafer et al. | 66/193 |
| 4,411,754 | 10/1983 | Kaetsu et al. | 204/159.15 |
| 4,425,395 | 1/1984 | Negishi et al. | 427/389.9 |
| 4,447,590 | 5/1984 | Szycher | 528/76 |
| 4,460,369 | 7/1984 | Seymour | 604/897 |
| 4,476,697 | 10/1984 | Schafer et al. | 66/193 |
| 4,483,759 | 11/1984 | Szycher et al. | 424/78 |
| 4,493,869 | 1/1985 | Sweeny et al. | 428/201 |
| 4,496,535 | 1/1985 | Gould et al. | 204/19 |

PERFUME PATCH

CROSS REFERENCE TO RELATED APPLICATIONS

This is a continuation of co-pending application Ser. No. 095,055 filed on Sept. 9, 1987, now abandoned, which is a continuation-in-part application of prior application U.S. Ser. No. 932,696, filed Nov. 19, 1986, now abandoned, entitled "Long Lasting Perfume Patch", which is a continuation-in-part application of prior application U.S. Ser. No. 768,623 filed on Aug. 23, 1985, entitled "Drug Release System", now U.S. Pat. No. 4,638,043 and of prior application U.S. Serial No. 726,809 filed on Apr. 25, 1985 entitled "Anisotropic Wound Dressing" and now abandoned, which are both continuation-in-part applications of prior application U.S. Ser. No. 670,810, filed Nov. 13, 1984, entitled "Drug Dispensing Wound Dressing", now U.S. Pat. No. 4,614,787.

BACKGROUND OF THE INVENTION

This invention relates to a perfume patch or fragrance-emitting article, and more particularly, to a polyurethane article containing a fragrance oil which is released at a controlled rate, and a method of making the same.

Various compositions and devices meant to release a fragrance over a long period of time are well known. The fragrances employed include both aromatic and perfumed compositions. An early form of such a device, and one still in use, was a pomander made by studding an apple or orange with cloves and useful as a garment sachet. Another approach still in use is to enclose dried leaves or flower petals in a perforated bag, box or other container. More recently, various solid substrates such as waxes or polymeric materials have been impregnated with fragrances for use, for example, as room fresheners. In such applications, a steady and controlled rate of release of the fragrance from the substrate is a desirable attribute. The uses of waxes or polymeric materials as substrates or carriers has the further advantage that the fragrance-containing materials can readily be formed or cut into virtually any desired shape or size.

As specific examples of the known materials described above, U.S. Pat. No. 3,567,119 to Wilburt discloses a method for incorporating fragrance compounds, oil bouquets or other agents into polymeric or natural materials so that the fabricated product possesses the properties imparted by the agent or agents for a long period of time; this method requires the use of surfactants for incorporating the agents and the duration of the agent in the fabricated product is enhanced by employing antioxidants and/or ultraviolet radiation absorbers. U.S. Pat. No. 3,303,046 to Chebiniak et al describes a composition containing pores, which express liquid upon application of pressure, formed from mixing an aqueous latex of a polymer with a plasticizer and heating to produce an aqueous composition containing dispersed droplets or plasticizer in which a coloring material may be dispersed. U.S. Pat. No. 4,493,869 to Sweeney et al describes fragrance-releasing appliques that provides a transparent or translucent substrate bearing microcapsules containing the fragrance in a binder on one surface. U.S. Pat. No. 4,254,179 to Carson et al describes a method and apparatus for impregnating a porous foam product with a fragrance that can be released over an extended period of time. U.S. Pat. No. 4,257,176 to Hartung et al describes an insole for footwear that has an odor masking or malodor counteractant material dissolved, trapped or encapsulated in a somewhat resilient resin coating through which it will progressively migrate or bleed under application of foot loads, foot perspiration and elevated foot temperatures to the surface of the coating to be released into the footwear to mask or counteract foot odors. U.S. Pat. No. 4,226,944 to Stone et al discloses fragrance-emitting articles comprising a polyurethane foam containing a particulate filler and a fragrance material, and a method of making such an article.

Each of the known compositions have some disadvantage such as high cost, inadequate rate of release of the fragrance, difficulty in forming and maintaining a desired shape, difficulty in preserving the quality of the fragrance in the formulation of the encapsulating product and so on. Processing conditions such as heat, pressure and chemical agents used in processing such as surfactants, water, solvents, etc., make it difficult to maintain the integrity of the desired fragrance. These disadvantages have led to a continuing search for improvements in fragrance-releasing compositions.

Most particularly, it is desired to have a perfume-emitting article suitable for wearing on any part of the body where one would normally dab perfume. In addition, it is desired to have a perfume-emitting article that may be used as, for example, a room deodorizer, and for that purpose, may be adhered to a wall or other object in the room. Another useful purpose for this perfume-emitting article is as an inclusion in a magazine in a pouch or on a postcard, where it provides a sample of the fragrance contained in the article.

With any of these uses, this article must be able to release a fragrance for an extended period of time. It is necessary that such an article remain adhered where it is positioned during the time fragrance is released. With some uses, however, for example when the article is used as a perfume patch or a room deodorizer, after all the fragrance has been released, the article must be removed.

Many fragrances used in known perfume-emitting articles, especially oil-based fragrances, will migrate through the adhesive layer that attaches the article to its position on a surface. The fragrance oil mixes with the adhesive, and plasticizes the adhesive, making it less cohesive and more sticky. The internal strength of the adhesive is reduced considerably. When it is desired to remove the patch, portions of the plasticized adhesive remain on the surface to which the patch had been attached. Such an article is totally unacceptable for the adhesive residue appears unsightly, picks up dust, and if it is on the skin, is uncomfortable and objectionable, necessitating washing the skin to remove the plasticized adhesive.

Accordingly, an object of the present invention is to produce a fragrance-emitting article or perfume patch which can be attached to a surface or any part of the body, and which will release fragrance for an extended period of time.

It is another object of the present invention to provide a perfume patch and a method of making such a perfume patch comprising a polyurethane containing a fragrance oil, which patch can be attached to any surface or worn on essentially any part of the body and will emit fragrance for an extended period of time.

It is an object of the invention to provide a perfume patch into which a fragrance oil may be dispersed without degrading the fragrance oil and the quality of the fragrance emitted.

Another object of the present invention is to provide a perfume patch, and a method of making such a perfume patch, that will remain attached in position on a surface during the entire time the fragrance is released, and when removed, will be cleanly removed from the surface.

Still another object of the present invention is to provide a perfume patch, and a method of making such a perfume patch, that will not leave traces or residue of the adhesive on the surface to which the patch had been attached.

It is a further object of the present invention to produce a fragrance-emitting article which can be produced at a low cost, provides an adequate rate of release of the fragrance, and can be shaped as desired.

Yet another object of the present invention is to provide an inexpensive means to enable potential perfume customers to sample the actual fragrance of a perfume and/or removably apply the perfume to the body.

Still another object of the invention is to provide an inexpensive yet effective means for disseminating sample quantities of perfume through the mail and/or as magazine inserts in a structure which can be opened to release the fragrance and which means can be removably applied to the body to enable the perfume to be sampled over an extended period of time.

SUMMARY OF THE INVENTION

The present invention is a perfume-emitting article or perfume patch including a fragrance-emitting layer or member comprising a fragrance oil dispersed within an ultra-thin polyurethane membrane which may be on a support. A layer of adhesive may be provided if it is desired that the article be applied to a surface. A barrier layer may be disposed between the fragrance-emitting layer or member and the adhesive layer to prevent migration of the fragrance oil from the fragrance-emitting layer or member to the adhesive layer, especially when it is desired that the patch be removable at a later time. Once the patch is applied to the surface, it will remain and release fragrance for an extended period of time. Upon removal of the patch, no adhesive residue remains on the surface when a barrier layer is used. A support layer may optionally be provided to improve the patch's dimensional stability and strength and to facilitate its handling and application. The support layer may be a reinforcing fabric with the fragrance-emitting layer or it may be a separate layer.

A patch so formed may be sealed in an aluminum foil pouch or applied to a postcard and disseminated to potential perfume customers either in person or through the mails. The layer or member of the patch which contains the fragrance oil is sufficiently permeable so that some fragrance will be released and its scent will be detectable.

In one most important embodiment of the method for making the perfume patch of the present invention, an oligomer is formed comprising a diisocyanate, a macroglycol and a chain terminator. An odorless photoinitiator and a fragrance oil are added to the oligomer, forming a mixture which is then applied to a polyethylene film having an adhesive coating on the other surface thereof. The oligomer layer containing the fragrance oil and the photoinitiator is subjected to ultraviolet radiation to cure the oligomer. A patch of the desired size and shape is prepared. A release liner may optionally be applied to the side of the patch on which the adhesive is found.

According to another important embodiment of the method of making the perfume patch of the present invention, an oligomer is formed comprising a diisocyanate, a macroglycol and a chain terminator. An odorless photoinitiator and fragrance oil are added to the oligomer, forming a mixture which is then applied to a support paper. The oligomer-coated paper is transported to an area in which a knitted reinforcing fabric is introduced, and the two travel through kiss, or press, rolls so that the fabric is gently embedded in the oligomer film. The oligomer containing the fragrance oil and the photoinitiator and further having the fabric is subject to ultraviolet radiation to cure the oligomer into a polyurethane containing a fragrance oil. A patch of the desired size and shape is prepared. A barrier layer comprising a medical grade, transparent occlusive polyethylene film with a thickness of 0.025–0.125 mm is applied to the exposed side of the fragrance-emitting layer by an adhesive or by other suitable means and a hypoallergenic pressure sensitive adhesive is applied to the exposed side of the barrier layer so that the patch may be applied to a surface. A release liner may optionally be applied to the side of the patch on which the adhesive is found.

These and other objects of this invention will become apparent to those skilled in this art form from the following detailed description, together with the drawing and the example below.

DETAILED DESCRIPTION OF THE INVENTION

The present invention is a fragrance-emitting member or layer which may optionally be used in conjunction with other supporting layers to form a composite article. In a most important embodiment of the invention, the perfume patch is a polyethylene sheet having a fragrance-emitting layer or member on one side and an adhesive layer on the other side. The fragrance-emitting member can be used for many purposes and in many places where diffusion will cause the scent of the perfume to be released from the member to the air. In the following description, the fragrance-emitting article will be described in reference to a preferred embodiment, that of a perfume patch. This embodiment is merely illustrative, and is not meant to be limiting.

The fragrance-emitting layer or member of the present invention comprises an actinic radiation cured polyurethane layer into which a fragrance oil is dispersed. The preferred formulation of the member is the reaction product of a diisocyanate and a macroglycol in the presence of a suitable catalyst which results in an isocyanate terminated prepolymer. The prepolymer is then reacted with a chain terminator, preferably an acrylyl chain terminator, to form an acrylyl terminated polyurethane oligomer. Suitable components for this oligomer are described in U.S. Pat. No. 4,483,759 to Szycher et al entitled "Actinic Radiation Cured Polyurethane Acrylic Copolymer", the teachings of which are incorporated herein by reference. A photoinitiator is then admixed with the foregoing components, and the desired fragrance oil is added to the mixture.

Isophorone diisocyanate (IPDI) is the preferred diisocyanate for use in the present invention and has the following formula:

IDPI is preferred in the present invention because IPDI is a liquid at room temperature, thus enabling the oligomer formed therefrom to easily form a coating layer on either the polyethylene film or the backing fabric. Additionally, oligomers in which IPDI is a reactant cure to a clear product. Furthermore, such oligomers are curable by actinic radiation, which means that there is no appreciable temperature rise while the oligomer is being cured and forming a layer. It should be noted that an appreciable temperature rise could destroy or modify the fragrance oil contained within this layer.

The macroglycol preferred for use in the present invention is polypropylene glycol (PPG), preferably having a number average molecular weight in the range 500-5000 and, more preferably 1000-3000 and having the following molecular structure:

where n is an integer selected to provide the desired molecular weight. PPG is preferred because it is a liquid at room temperature and it reacts with the IPDI to form an oligomer. Other high molecular weight glycols such as polyethylene glycol (PEG) may be employed but PEG is a solid at room temperature and a feasible rate of reaction would require heating. As used herein, the term macroglycol has reference to any glycol having a molecular weight in excess of 500 Daltons.

A preferred catalyst is dioctyl tin dilaurate.

The chain terminator used in formulating the products of the invention should have both hydroxyl and vinyl functional groups and it is preferably an acrylyl compound such as hydroxyethylacrylate or hydroxyethylmethacrylate. Hydroxyethylmethacrylate (HEMA) is most preferred for use as the chain terminator and has the following formula:

The preferred polyurethane oligomer of the invention has the following structural formula:

A photoinitiator is then added to the oligomer mixture to accelerate curing of the oligomer mixture to form the polymer by actinic light This is particularly desirable if the mixture is to be cured at room temperature. Furthermore, because the polyurethane will also encompass a fragrance oil whose scent is to be emitted from the patch, it is desirable that the photoinitiator chosen for use in the present invention not have any odor or smell which will compete with that of the fragrance oil. The preferred photoinitiator is 2,2-dimethoxy-2-phenylacetophenone, which has the following structural formula:

The desired fragrance oil is then added to the oligomer-photoinitiator mixture Any perfume or fragrance oil which is chemically unreactive to the system may be added, as well as a deodorizing material Because the curing process proceeds by exposure to actinic light, most preferably ultraviolet light, a wide variety of fragrance oils can be incorporated into the perfume patch of the present invention. The process does not require heat and, therefore, no cooling of any reaction mixture is required prior to the addition of an oil having a fragrance highly susceptible to degradation by heat. The present invention is superior for producing a perfume patch because most fragrance oils are not heat stable and temperatures normally used to produce a polyurethane would destroy the quality of the fragrance. Fragrance oils which are very low boiling or heat-sensitive, and would thus be lost or destroyed during an exothermic reaction generally used in polyurethane production, may be used in the present invention. Fragrance oils are usually complex mixtures. The use of oil having fragrances containing esters, terpenes, lactones, aldehydes, and/or ketones and preferably in the form of a fragrance essential oil is preferred.

The amount of fragrance oil can be varied over a wide range, depending on such factors as the intensity of the odor desired for a given application and the desired useful life of the fragrance-emitting article. Generally, it will be desired to incorporate a high level of fragrance oil in order to obtain a long useful life, subject to the requirements of processability (i.e. curing) and strength of the article in a patch. By way of illustration, we have found that the fragrance oil levels of from about 5% by weight to about 20% by weight of the oligomer in the reaction mixture are useable.

In some applications, it may be desirable to add a pigment to the fragrance-emitting layer so that the perfume patch has a pleasing decorative appearance. Pigments may be added prior to curing in the amount of up to 5% by weight of the oligomer. For example, cosmetic pearl pigment, $TiO_2$ coated mica, may be added in the amount up to 5% by weight of the oligomer for decorative articles.

The fragrance-emitting layer is then photocured by exposure to actinic light. Actinic light useful herein for curing is ultraviolet light and other forms of actinic radiation which are normally found in radiation emitted from the sun or from artificial sources such as type RS sunlamps, carbon arc lamps, xenon arc lamps, mercury vapor lamps, tungsten halide lamps and the like. Ultraviolet radiation having a wavelength from about 200 to about 400 nanometers is suitable. The curing period is very short, usually between 0.5 and 15 seconds when the composition is exposed to actinic light having a power density of 10 kilowatts per square feet.

The cured polyurethane layer in which a fragrance oil is dispersed is clear, soft and elastic. This resulting article is also thin, strong and keeps its shape. The layer may be rolled and stored until it is to be used or it may be further processed into perfume patches as described hereinafter. The layer is stable during storage.

The layer may be cut to any desired shape and size in order to be used on various surfaces or parts of the body, such as on the arm, behind the ear or other suitable locations on the skin. For example, a suitable patch formed from the fragrance-emitting layer is circular in shape and about 1.27 cm in diameter. When used on skin, body heat plays a role in accelerating the rate at which fragrance is emitted from the polyurethane layer. It has been found that the layer emits a fragrance for several hours.

Figure 1:
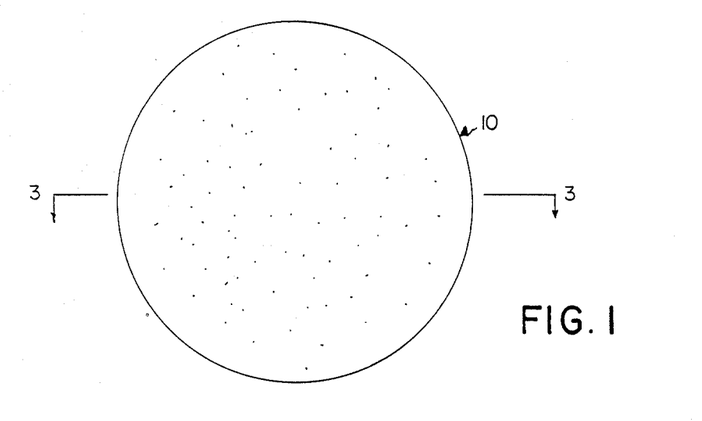
FIG. 1 is a view of the perfume-emitting article of the present invention which has been made into a pressure sensitive, self-adhesive perfume patch.

The fragrance-emitting layer may be applied to a surface by a pressure sensitive adhesive such as an acrylate adhesive. This embodiment, as shown in FIG. 1, would be useful on a postcard as a magazine insert or for dissemination through the mails. Alternatively, if the article is to be applied to a person, the adhesive used should be hypoallergenic. A suitable adhesive is an ethyl acrylate/vinyl pyrrolidone mixture.

Generally, however, it is desirable that the fragrance-emitting layer have some type of support. Reinforcement of the layer by a support layer improves its dimensional stability and strength, facilitating handling and application of the article. It also permits higher levels of fragrance oil to be utilized than would be possible without the reinforcement since the tear strength of an unreinforced polyurethane decreases with increasing levels of fragrance oil present.

In one important embodiment, the support is a reinforcing fabric in the fragrance-emitting layer. An open mesh knitted fabric is used as the reinforcement and additionally will give the layer anisotropic properties. By anisotropic is meant that the fabric stretches more in one direction than in the other. This characteristic is imparted to the layer when the fabric is in the cured polyurethane. It allows the layer to stretch in the direction of the surface, for example skin, to which it is applied. The term "knitted" is intended to describe the process to form textile material by interlacing yarn or thread in a series of connected loops with needles. The knitted reinforcing fabric can be made out of any textile material, such as a polyester. Polyester, however, is considered to be expensive relative to other very porous fabrics, such as certain nylon fabrics. A desirable fabric is a warp knit 15 denier nylon-6 tricot, heat set material. One such fabric is sold by Gehring Textiles, New York, New York and is formed from Nylon 6 yarns. Any fabric of the proper geometry, however, which is biocompatible may be used.

Preferred knitted fabrics have the following characteristics. The openings or interstices in the fabric are hexagonal, of a size ranging from 0.5 mm to 4 mm across, although preferably they are 2 mm in size. The fabric is knitted from the yarns having a diameter in the range of 0.025 to 0.203 mm, although preferably with a diameter of 0.1 mm. The term "yarn" as used herein is intended to describe both yarns formed from fibers or filaments twisted together and yarns formed from monofilament fibers. The yarn itself need only have modest elongation properties. The stretch characteristics of the fabric are achieved by the mechanical processing and geometry. In its preferred embodiment, the ratio of the diameter of the thread to the size of the void area is 0.1:2, or 5% thread to 95% void area.

Figure 2:
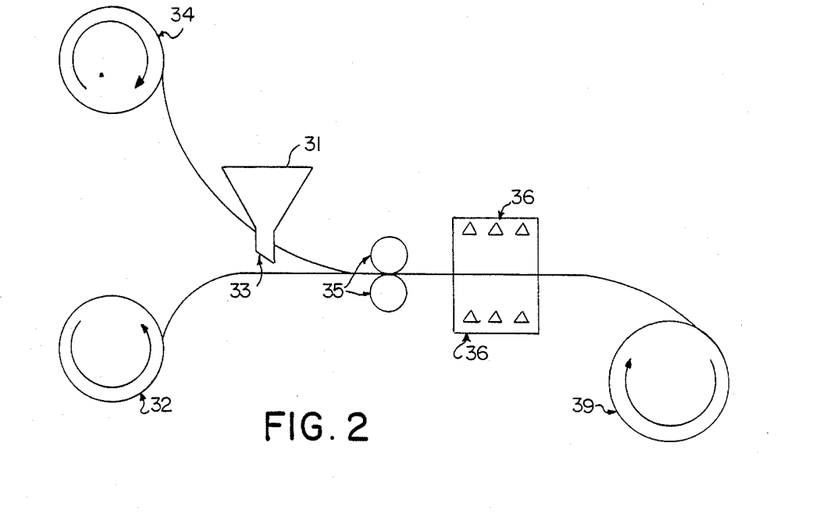
FIG. 2 is a diagram illustrating a method of making the fragrance-emitting layer of the perfume patch of the present invention.

The process to form this embodiment is shown in FIG. 2. Once the oligomer, the photoinitiator and the fragrance oil are combined as described above, the mixture is placed in a dispenser 31 from which it is applied to a supporting paper 32 with any conventional means, such as a coating knife 33. The paper provides support for the mixture prior to its actinic radiation curing. The coated paper and the reinforcing fabric 34 are transported to press or kiss rolls 35 in which the fabric is gently embedded into the mixture and becomes coated with the mixture. The mixture coats the fabric and forms a film that fills the interstices. The thickness of the cured polyurethane membrane or film is in the range of about 0.0254 mm to 0.254 and preferably is about 0.076 mm.

Figure 3:
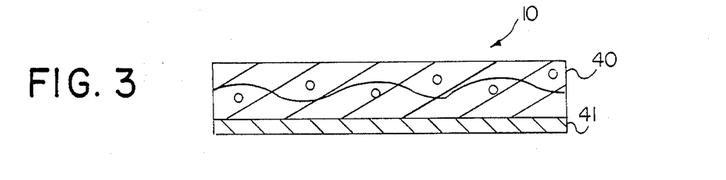
FIG. 3 is a cross-sectional view of the perfume patch in FIG. 1, taken along the cut at Line 3—3 exposing the layers of the patch.

In order to form a perfume patch 10 from this embodiment, a pressure sensitive adhesive 41 such as an acrylate adhesive conventionally used for wound dressings or bandages may be spread over one surface of the fragrance-emitting layer containing the reinforcing fabric 40. This embodiment of the perfume patch of the present invention is shown in FIG. 3.

If the perfume patch is to be applied and never removed, for example on a magazine insert to provide a sample of a perfume's fragrance, the layer of adhesive is applied to the fragrance-emitting layer to form a patch and the patch is applied in position. Often, however, the patch will be removed when the fragrance is depleted, such as on a stick-up room deodorizer or a perfume patch for the body, and it is then necessary that measures be taken to prevent leaving residue of the adhesive on the place that the patch was situated. It has been found that, in use, certain fragrance oils tend to migrate through the adhesive, in addition to releasing fragrance through the air. Upon its migration through the adhesive, the fragrance oil will plasticize the adhesive and cause it to become gummy and come off onto the wearer's skin. A barrier layer prevents migration it the fragrance oil to and through the adhesive so as to prevent the adhesive from coming off onto the wearer's skin when the patch is removed.

Figure 4:
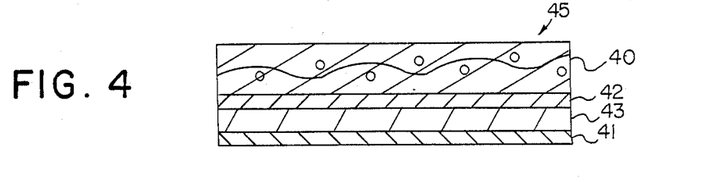
FIG. 4–8 are cross-sectional views of alternate embodiments of the perfume patch of the present invention.

In the perfume patch 45 of the present invention as shown in FIG. 4, a barrier layer may be applied to prevent the adhesive from coming off onto the surface to which the patch is applied. The barrier layer 43 is adhered to the fragrance-emitting layer 40 containing the reinforcing fabric by a hypoallergenic adhesive 42. A second adhesive layer 41 will be applied to the exposed side of the barrier layer 43. Of course, the second adhesive layer 41 must be biocompatible if used on a perfume patch that will contact the skin.

Generally, the barrier layer 43 will be a transparent occlusive film that does not allow gas or liquids to permeate, such as a polyethylene or polypropylene film. A barrier layer as used in the present invention will generally be 0.025 to 0.125 mm thick. A thicker layer may be stiff and uncomfortable to the wearer. A preferred barrier layer is a medical grade, transparent occlusive film comprising a polyethylene with adhesive coated on one side, sold by Fasson Medical Products Inc., of Painesville, Ohio under the tradename "MED 3 Mil Polyethylene 57105". In this particular product, the adhesive coated side of the barrier layer faces the fragrance-emitting layer and obviates the need for the pressure sensitive adhesive layer used next to the fragrance-emitting layer.

In another important embodiment of the present invention, a reinforcing fabric is not provided within the fragrance-emitting layer and instead, a separate support layer is provided for reinforcement. A support layer may comprise a film of polyethylene or polypropylene having a thickness of approximately 0.025 to 0.125 mm. The preferred support layer is of polyethylene. Generally, polyethylene sheets do not have good adhesion properties. Consequently, the oligomer used in the present invention will not adhere to the polyethylene sheet. It is therefore necessary to use an adhesive or other methods, such as treating the surface of the polyethylene support layer, to make the surface receptive to be attached to the fragrance-emitting layer.

Figure 5:
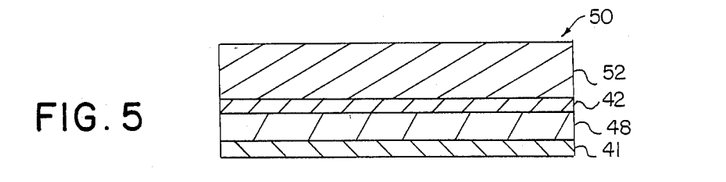

If adhesive is used, the perfume patch 50 comprises, as shown in FIG. 5, a fragrance-emitting layer 52, a layer of pressure sensitive adhesive 42, the support layer 48, and a second layer of pressure sensitive adhesive 41 to attach the patch to a surface. In this embodiment, the support layer 48 will act not only as a support, but also as a barrier layer to prevent the adhesive from coming off onto the surface to which the patch is attached.

Figure 6:
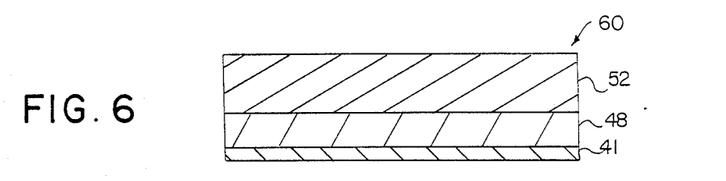

The polyethylene support layer may be applied to the fragrance-emitting layer by a non-adhesive process. For example, a corona discharge treatment may be used. This method is well known in the printing industry. A large voltage differential is applied across a gap between electrodes, forming a plasma arc. The plasma arc is applied to the polyethylene sheet, resulting in free radicals being produced on its surface. The free radicals formed oxidize the surface of the polyethylene sheet, making the surface receptive to be attached to the oligomer. The fragrance-emitting layer is applied to the thus treated polyethylene support layer and becomes bonded thereto. If the support layer is attached to the fragrance-emitting layer by corona discharge treatment, the resulting perfume patch 60 would comprise a fragrance-emitting layer 52, a support layer 48 and a layer of pressure sensitive adhesive 41 to attach the patch to a surface. This embodiment is shown in FIG. 6. Again, in this embodiment, the support layer 48 also acts as a barrier layer to prevent migration of the fragrance oil resulting in the adhesive becoming plasticized.

Another suitable support layer is a polyurethane layer. The preferred polyurethane supporting layer is SPANDRA ®, a trademark of Thermedics, Inc. for a wound dressing. The SPANDRA ® wound dressing includes a polyurethane which is the reaction product of (1) isophorone diisocyanate, (2) a macroglycol having a molecular weight in the range of 500–5000 molecular weight units, and (3) a chain terminator containing hydroxyl and vinyl groups and is further described in U.S. Ser. No. 726,809, entitled "Anisotropic Wound Dressing", filed Apr. 25, 1985 in the name of Michael Szycher et al. The teachings of this application are incorporated herein by reference. This oligomer is cured by exposure to ultraviolet light to form a solid polyurethane film.

Figure 7:
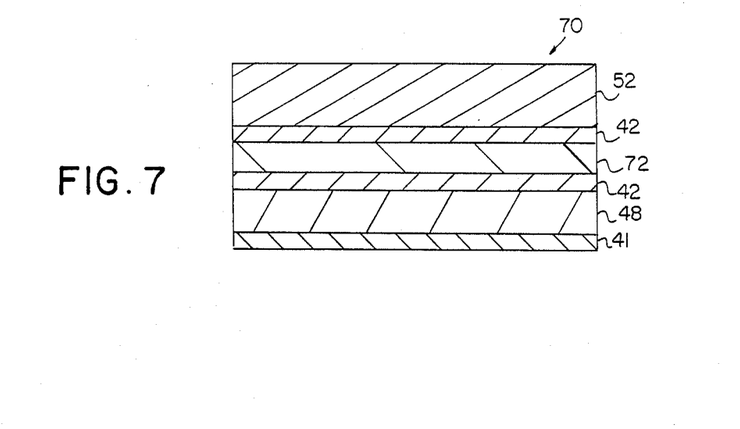

The polyurethane support layer is applied by adhesive or other suitable means to the fragrance-emitting layer. If adhesive is used for the application, a barrier layer should be used to prevent residues of the plasticized adhesive from remaining on the surface where the patch is positioned. As shown in FIG. 7, a perfume patch 70 according to this embodiment comprises a fragrance-emitting layer 52, a layer of adhesive 42, a support layer of polyurethane 72, a second layer of adhesive 42, a barrier layer 48, and a third layer of adhesive 41 to apply the patch to a surface.

Figure 8:
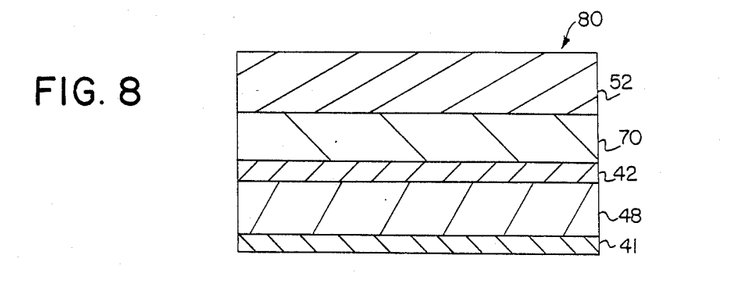

If a non-adhesive process is used to apply the fragrance-emitting layer to the polyurethane support layer, the patch 80 will comprise a fragrance-emitting layer 52, a support layer of polyurethane 72, a layer of adhesive 42, a barrier layer 48 and a second layer of adhesive 41 for application of the patch 80 to a surface. This embodiment is shown in FIG. 8.

The perfume patch of the present invention is further described with reference to the following non-limiting example:

EXAMPLE

In a nitrogen blanketed chemical reactor, 24.5% by weight of IPDI, and 57.2% by weight of 1,000 MW PPG, and 0.1% by weight of dioctyl tin dilaurate are heated at 85° C. for one hour, under continuous agitation. Following this initial reaction, to the above mixture 18.0% by weight of hydroxyethyl methacrylate is added quickly, and the complete mixture is heated at 65° C. for three hours.

At the end of this period, a clear liquid is obtained, called a urethane oligomer. To this mixture, 0.25% by weight of 2,2 dimethoxy-2 phenylacetophenone is dissolved, resulting in a stable mixture ready for UV curing (a fully compounded oligomer). About 85 ml of the fully compounded oligomer is charged into dispenser 31. At this time, about 15 ml of concentrated oil of geraniol (essence of rose) is added.

The mixture is fed through dispenser at a rate of 10–20 linear feet per minute and a film is drawn on a release paper or polyethylene substrate by a coating knife, roller or coating rod, and a nylon-6 reinforcing fabric is gently embedded in the film by the action of kiss or press rolls.

The resulting composite is then irradiated by ultraviolet light, typically between 200 and 400 nanometers in wavelength at an energy level of 10 kilowatt/seconds per square foot.

The cured composite comprising a knitted reinforcing fabric in a polyurethane is then laminated to a barrier layer having a thickness of 0.07 mm and comprising a polyethylene film by an adhesive coating on the side facing the cured composite. A hypoallergenic pressure sensitive adhesive is applied to the other side of the barrier layer. In this instance, an adhesive transfer film/release liner is used and the paper substrate on which the composite was formed is stripped and discarded.

With any of the embodiments described above, a release liner may be applied to an exposed adhesive layer for easy transport of the perfume patch when it is not in use. Once the patch is positioned in place, it will release fragrance continually for an extended period of time.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A perfume patch comprising a fragrance-emitting member comprising a polyurethane consisting essentially of
   (1) a diisocyanate;
   (2) a glycol having a molecular weight between the range of 500–5000 molecular weight units;
   (3) an acrylyl chain terminator having a molecular weight between the range of 40 and 200 molecular weight units; and
   (4) a photoinitiator into which a perfume is dispersed; and
   (5) a barrier layer adhered to the fragrance-emitting member.

2. The perfume patch of claim 1 wherein in said fragrance-emitting member, said perfume is selected from the group consisting of fragrances and deodorizing materials, and said perfume is in the form of an essential oil which is dissolved in the polyurethane prior to cure in the amount of about 5% to 25% by weight of the polyurethane.

3. The perfume patch of claim 1 further comprising a layer of pressure sensitive adhesive on the side of the perfume patch that will be adhered to a surface.

4. The perfume patch of claim 1 wherein the fragrance-emitting member is comprised of a polyurethane which consists essentially of the reaction product of
   (1) isophorone diisocyanate;
   (2) polypropylene glycol; and
   (3) hydroxyethymethacrylate.

5. The perfume patch of claim 1 further comprising a layer of release liner on the exposed side of the pressure sensitive adhesive.

6. The perfume patch of claim 3 wherein the layer of pressure sensitive adhesive is a hypoallergenic adhesive.

7. The perfume patch of claim 1 further comprising a cosmetic pearl pigment in the amounts of up to 5% by weight of the polyurethane of the fragrance-emitting member.

8. The perfume patch of claim 1 wherein said barrier layer comprises a polyethylene film having a thickness of from 0.025 to 0.125 mm.

9. The perfume patch of claim 1 wherein said photoinitiator of the fragrance-emitting member is 2,2-dimethoxy-2-phenylacetophenone.

10. The perfume patch of claim 1 further including support means adhered between the fragrance-emitting member and the barrier layer.

11. The perfume patch of claim 10 wherein the support means comprises a support layer of polyurethane.

12. The perfume patch of claim 11 wherein the support layer of polyurethane comprises the reaction product of isophorone diisocyanate, a macroglycol having a molecular weight in the range of 500 to 5000 molecular weight units and a chain terminator containing hydroxyl and vinyl groups.

13. The perfume patch of claim 10 wherein the support means comprises a knitted reinforcing fabric, said knitted reinforcing fabric defining a network of interstices having a void area in the range of 0.5 mm to 4mm across and is formed from yarns having a diameter in the range of 0.025 to 0.203 mm, and wherein said fragrance-emitting member includes a film filling said interstices, said film having a thickness in the range of about 0.0254 mm to 0.254 mm.

14. The perfume patch of claim 10 wherein the support means comprises a support layer of polyethylene having a thickness of from 0.025 to 0.125 mm.

15. A method of distributing perfume as samples so that it can be removably worn by a wearer to test its fragrance comprising:
   providing a structure including a polymer layer into which a perfume is dispersed, a barrier layer adhered to one side of the polymer layer and an adhesive layer attached to the exposed side on the barrier layer, said adhesive layer allowing for the removable attachment of the structure to a surface; and
   distributing the structure so provided to wearers so that it can be removably attached to the wearer's skin by means of the adhesive layer to test the fragrance and to allow for removal at will.

16. The method of claim 15 further comprising the step of:
   placing the structure so provided in means for containing the structure so that the step of distributing the structure which follows is facilitated.

17. The method of claim 15 wherein the polymer layer of the structure comprises an actinic radiation cured polyurethane which consists essentially of the reaction product of
   (1) a diisocyanate;
   (2) a glycol having a molecular weight between the range of 500–5000 molecular weight units;
   (3) an acrylyl chain terminator having a molecular weight between the range of 40 and 200 molecular weight units; and (4) a photoinitiator into which a perfume is dispersed.

18. The method of claim 17 wherein the polymer layer is comprised of a polyurethane which consists essentially of the reaction product of
   (1) isophorone diisocyanate;
   (2) polypropylene glycol; and
   (3) hydroxyethymethacrylate.

19. The method of claim 15 wherein the perfume in the polymer layer is selected from the group consisting of fragrances and deodorizing materials, and said perfume is in the form of an essential oil which is dissolved in the polymer prior to cure in the amount of abut 5% to 25% by weight of the polymer.

20. The method of claim 15 further comprising the step of adhering a layer of release liner on the exposed side of the adhesive layer prior to distributing the structure.

21. The method of claim 15 wherein the structure provided further includes support means.

22. A method for a person to sample perfume comprising:
   obtaining a structure including a polymer layer into which a perfume is dispersed, a barrier layer adhered to one side of the polymer layer and an adhesive layer attached to the exposed side of the barrier layer, the adhesive layer allowing for the removable attachment of the structure to the person's skin;
   applying the structure to the person's skin;
   removing the structure as desired.

23. The method of claim 22 wherein the polymer layer of the structure comprises an actinic radiation cured polyurethane which consists essentially of the reaction product of
   (1) a diisocyanate;
   (2) a glycol having a molecular weight between the range of 500–5000 molecular weight units;
   (3) an acrylyl chain terminator having a molecular weight between the range of 40 and 200 molecular weight units; and
   (4) a photoinitiator into which a perfume is dispersed.

24. The method of claim 23 wherein the polymer layer is comprised of a polyurethane which consists essentially of the reaction product of
   (1) isophorone diisocyanate;
   (2) polypropylene glycol; and
   (3) hydroxyethymethacrylate.

25. The method of claim 22 wherein the perfume in the polymer layer is selected from the group consisting of fragrances and deodorizing materials, and said perfume is in the form of an essential oil which is dissolved in the polymer prior to cure in the amount of about 5% to 25% by weight of the polymer.

26. The method of claim 22 further comprising the step of adhering a layer of release liner on the exposed side of the adhesive layer prior to distributing the structure.

27. The method of claim 22 wherein the structure provided further includes support means.

* * * * *